United States Patent

Pitet et al.

[11] 4,188,387
[45] Feb. 12, 1980

[54] AMINO-ARYL 1,24-TRIAZINES USEFUL IN THE TREATMENT OF DIVERSE PAIN

[75] Inventors: Guy Pitet, Toulouse; Henri Cousse, Castres; Gilbert Mouzin, Castres; Antoine Stenger, Castres, all of France

[73] Assignee: Pierre Fabre S.A., France

[21] Appl. No.: 884,732

[22] Filed: Mar. 9, 1978

[30] Foreign Application Priority Data

Mar. 9, 1977 [FR] France ............... 77 07245
Feb. 17, 1978 [FR] France ............... 78 04822

[51] Int. Cl.² ............... C07D 253/06; C07D 413/10; A61K 31/53
[52] U.S. Cl. ............... 424/249; 424/248.51; 424/248.56; 544/112; 544/182
[58] Field of Search ............... 544/182, 112; 424/249, 424/248.51, 248.56

[56] References Cited

U.S. PATENT DOCUMENTS 3,948,894  4/1976  Lacefield ............... 544/182

Primary Examiner—John M. Ford
Attorney, Agent, or Firm—Gordon W. Hueschen

[57] ABSTRACT

The invention relates to new chemical compounds which can be used as analgesic drugs and their preparation.

The new chemical compounds have the general formula:

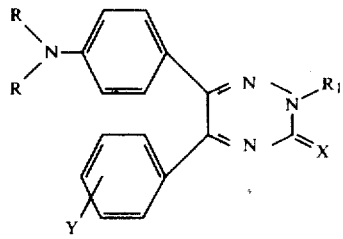

in which:
R is a lower alkyl
$R_1$, which is always other than H, is a linear or branched lower alkyl, an allyl, amino alkyl of type

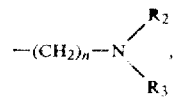

in which n=2 to 4, $R_2R_3$ represent a lower alkyl; they may also form a heterocycle with the nitrogen atom.
Y is a hydrogen, halogen, lower alkyl, alkoxy,

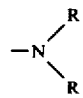

R being a lower alkyl.
The position of Y is variable on the ring.
X=oxygen or sulfur atom.

The drugs containing these active principles may be used in the treatment of rheumatismal disturbances and various pains.

24 Claims, No Drawings

AMINO-ARYL 1,24-TRIAZINES USEFUL IN THE TREATMENT OF DIVERSE PAIN

This invention, developed at the Pierre FABRE Research Center, concerns new chemical compounds which are members of the family of diaryl 1-2-4-triazines, their methods of preparation and their use in therapy. They are useful in particular for the treatment of rheumatismal ailments and various pains.

The invention also relates to pharmaceutical compositions containing these active principles.

These new drugs contribute to improving the treatment of rheumatismal and arthritic disturbances, some of the drawbacks of which are well known, particularly with reference to tolerance.

Access to the 5,6-diaryl-1-2-4-triazines is described by John G. ERICKSON in "The 1-2-3 and 1-2-4 triazines, tetrazines and pentazines," The Chemistry of Heterocyclic Compounds, Vol. 10, Intersciences Publishers, New York, 1956 (chapter II, pages 44 to 84).

Recent work of the LILLY Laboratory (U.S. Pat. No. 3,948,894 of Jan. 31, 1974, and Belgian Pat. No. BE 839,469 of Mar. 11, 1976) concerns compounds of similar structure, but the compounds in accordance with the present invention differ by the presence of a substituent $R_1$ in 2-position, this substitution being very important with respect to the pharmacological activity. As compared with the 1-2-4 triazine derivatives described in French patent 76.32162, hydrophilic groups were introduced either in position 2 or as substituent on the aryls.

The compounds in accordance with the invention have the general formula:

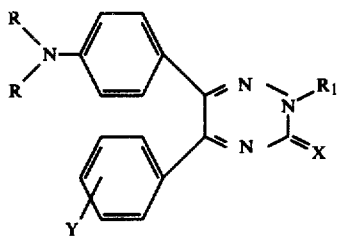

in which:
R = lower alkyl
$R_1$ = linear or branched lower alkyl, allyl or amino alkyl of the type:

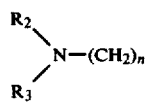

in which n=2 to 4, $R_2$ and $R_3$ represent a lower alkyl, $R_2$ $R_3$ may form with n a heterocycle
Y = H, halogen, alkyl, alkoxy,

R lower alkyl. The position of Y is variable on the ring. X = sulfur or oxygen.

These compounds are obtained by the action of semicarbazides or thiosemicarbazides on $\alpha,\alpha$-diketones.

The $\alpha,\alpha$-diketones are obtained by one of the following methods depending on the nature of the substituents:

(a) dimerization of the aldehydes in the presence of potassium cyanide

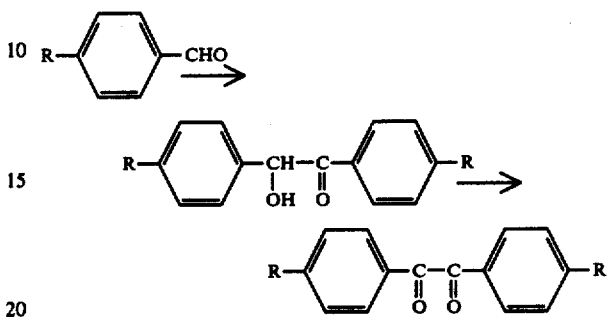

(b) The disymmetric $\alpha,\alpha$-diketones are obtained:
either by rearrangement of a symmetric diketone with a differently substituted aldehyde in the presence of potassium cyanide, or:
by dimerization in mixture of differently substituted aldehydes.

(c) Friedel and Craft's reaction between oxalyl chloride and an aromatic substrate, for example

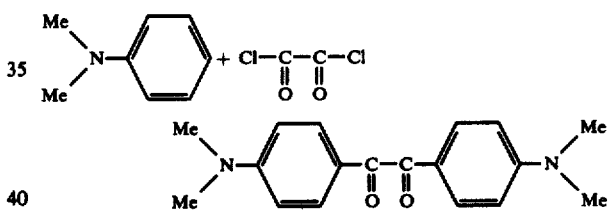

The 1-2-4 triazines which are the object of the invention are obtained in accordance with the reaction mechanism:

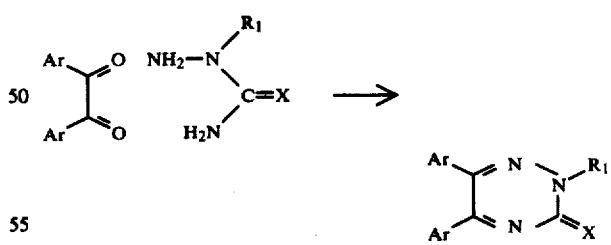

$R_1$ = H, lower alkyl

When $R_1$ is equal to H, the intermediate triazine is then N-substituted after activation of the N-H bond by concentrated NaOH, NaH, etc.

The following chemical compounds and their method of preparation are cited by way of illustration and not of limitation. For the sake of convenience they are designated by a code number in order to facilitate the presentation of the text and the description of the results of the experiments to which they are subjected.

EXAMPLE 1

2-methyl 3-oxo 5,6-di(paradimethylamino-phenyl) as. triazine (ST 729)

Procedure A 890 g (3 mols) of p-dimethyl amino-benzyl and 670 g of semicarbazide hydrochloride (6 mols) were introduced into a 10 liter reactor containing 3 liters of acetic acid. It was then heated for 2 hours at 115° C. The reaction mixture was cooled and poured into 12 liters of water with good agitation, and neutralized with about 2200 g of caustic soda, dissolved in 4 liters of water. The triazine precipitates, forming fine yellow crystals. The agitation is continued for 30 minutes and the suspension is then filtered. About 1000 g of triazine are recovered (quantitative yield) having the formula:

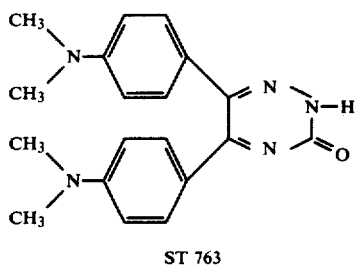

ST 763

Yellow crystals

Soluble in aqueous dilute bases and acids, poorly soluble in alcohol, benzene, methylene chloride, chloroform.
Insoluble in ether.
Melting point: 230° C.

By the action of methyl sulfate in concentrated alkaline solution the derivatives methylated in 2-position is obtained by using the phase transfer technique with catalysis by a quaternary ammonium, operating in the manner described below.

Two liters of 50% caustic soda, two liters of methylene chloride, 3.5 g of benzyl triethyl ammonium chloride and 334 g of triazine (1 mol) are added to a 10 liter reactor. 1.1 mol of methyl sulfate is then added within the course of five minutes.

The agitation is continued in the cold for two hours, whereupon the reaction mixture is poured into 8 liters of water with agitation and then set aside for 1 hour. The organic phase is recovered and washed with water until neutral. After drying over sodium sulfate, the organic phase is concentrated and then precipitated by the addition of hexane so as to obtain about 300 g of orangish-yellow crystals (yield 90%); this product can be recrystallized from N-propanol.

ST 729 has the formula:

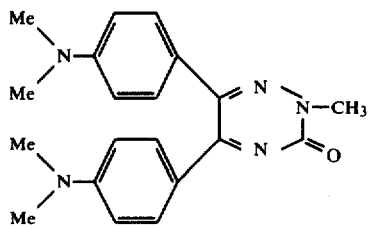

Yellow crystals insoluble in water, dilute bases, benzene, and ether.
Soluble in dilute acids, alcohol and methylene chloride.
Melting point: 204° C.

Procedure B:

ST 729 can be prepared directly by using, during the cyclization, the N-methyl semicarbazide having the formula:

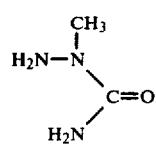

Thus, from one mol of 4-4'-bis(dimethylamino)benzyl and one mol of N-methyl semicarbazide of the above formula in acetic acid under reflux ST 729 is obtained in a yield varying from 50 to 70%. This second method of production makes it possible to confirm the structure of the derivative obtained by the manner of procedure and proves that the alkylation by the methyl sulfate takes place on the nitrogen in 2-position and not on the oxygen in 3-position. Furthermore, the derivative methylated in 3-position was prepared; it is different from ST 729.

EXAMPLE 2

2-methyl 3-oxo 5(orthochlorophenyl) 6(paradimethylaminophenyl) as. triazine (ST 746)

Prepared by the procedure A of Example 1, but using a disymmetric diketone, there is obtained:

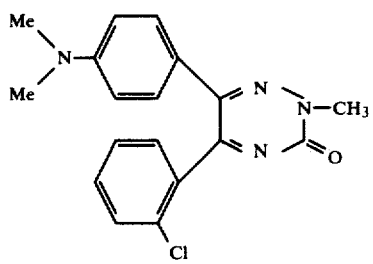

Orange crystals

Insoluble in water, dilute bases and ether.
Soluble in methylene chloride, benzene, alcohol, chloroform and dilute acids.
Melting point: 213° C.

In accordance with procedure A there is obtained as intermediate the derivative (ST 745) of the formula:

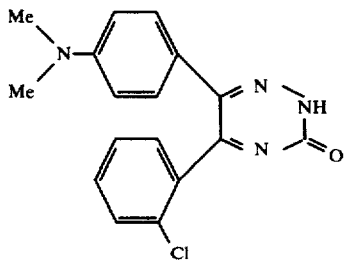

Orangy crystals

Insoluble in water, benzene, and ether.
Soluble in dilute bases and acids, ethanol, and methylene chloride.
Melting point: 260° C.

EXAMPLE 3

2-methyl 3-oxo 5(parachlorophenyl) 6(p-dimethylaminophenyl) as triazine (ST 761)

Starting from dimethyl-4-amino-4'-chlorobenzyl and methyl semicarbazide there is obtained

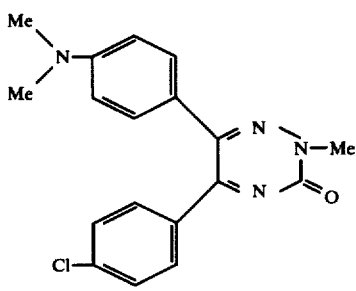

Orange crystals
Soluble in dilute acids, CH$_2$Cl$_2$, and chloroform.
Insoluble in water, dilute bases, and ether.
Melting point: 184° C.
This derivative can also be prepared by procedure A of Example 1.

EXAMPLE 4

2-methyl 3-oxo 5,6-di(paradiethylamino phenyl) as triazine (ST 771)

By treating 4,4'-bis(diethylamino)benzyl with semicarbazide in acetic acid under reflux, 3-oxo 5,6-di(paradiethylaminophenyl) as triazine (ST 770) is obtained as intermediate, it having the formula:

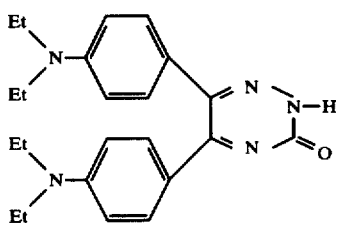

Yellow crystals
Soluble in dilute acids and bases, alcohol, benzene, and methylene chloride.
Melting point: 230° C.
By the action of methyl sulfate in alkaline solution on ST 770, ST 771 is obtained, of the formula:

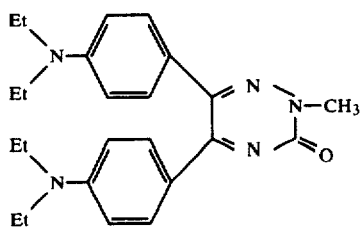

Yellow crystals

Soluble in dilute aqueous acids, alcohol, methylene chloride, and chloroform.
Insoluble in water, dilute bases, benzene, ether.
Melting point: 103°–104° C.

EXAMPLE 5

2 Ethyl morpholino 3-oxo 5,6 di(paradimethylaminophenyl) as. triazine (ST 767)

Prepared by treating ST 763 by an equimolecular quantity of sodium hydride and then by 2-chloroethyl N-morpholine, obtaining a product of the formula

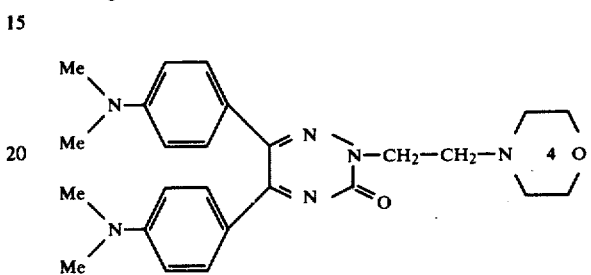

Orange crystals
Soluble in dilute aqueous acids, alcohol, methylene chloride, and chloroform.
Insoluble in water and dilute bases, benzene and ether.
Melting point: 196° C.

EXAMPLE 6

2-allyl 3-oxo 5,6-di(paradimethylaminophenyl) as triazine (ST 776)

By treating ST 763 in succession by an equimolecular quantity of sodium hydride and then with allyl bromide, there is obtained derivative ST 776, of the formula:

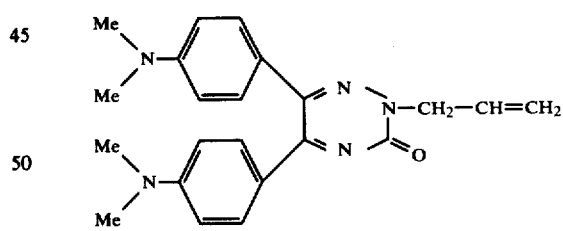

Yellow crystals
Soluble in dilute aqueous acids, alcohol, benzene, methylene chloride, and chloroform.
Insoluble in water, bases, and ether.
Melting point: 160° C.

EXAMPLE 7

2-[3-dimethylamino)propyl]3-oxo 5,6-di(paradimethyl aminophenyl) as triazine (ST 778)

By treating the ST 763, as previously but using dimethylaminopropyl chloride, there is obtained ST 778, of the formula:

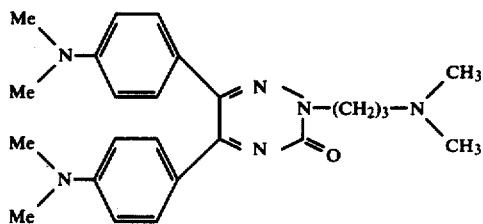

Orange crystals

Soluble in dilute aqueous acids, alcohol, benzene, methylene chloride, and chloroform.

Insoluble in water, dilute bases and ether.

Melting point: 174° C.

EXAMPLE 8

2-diethylaminoethyl 3-oxo 5,6(paradimethylaminophenyl) as triazine (ST 790)

By proceeding as previously, but using diethylamino ethyl chloride, there is obtained ST 790, of the formula:

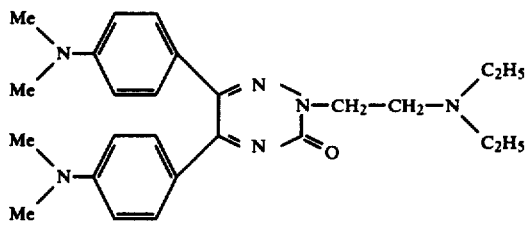

Orange crystals

Soluble in dilute aqueous acids, alcohol, benzene, methylene chloride, and chloroform.

Insoluble in bases, water, and ether.

Melting point: 167° C.

EXAMPLE 9

2-methyl 3-thione 5,6-di(paradimethylaminophenyl)as triazine (ST 811)

By treating ST 729 in solution with $P_2S_5$, there is obtained the derivative ST 811, of the formula:

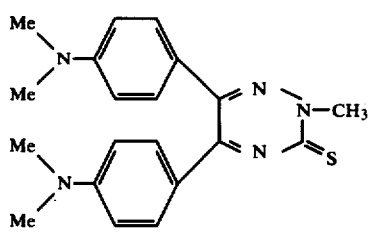

Red crystals

Soluble in aqueous dilute acids, alcohols, and methylene chloride.

Insoluble in water, aqueous bases, and ether.

Melting point: 220° C.

Remark:

By exchange reaction, oxidized derivatives of Examples 2 to 8 can be transformed into sulfur equivalents in 3 position by the action of $P_2S_5$, as in Example 9.

EXPERIMENTATION

The derivatives previously described were subjected to pharmacological and toxicological tests which made it possible to show interesting analgesic properties.

For the sake of convenience, the chemical compounds are designated by their code number.

(A) Toxicology

The toxicity study was carried out on the conventional mouse, weighing about 20 g.

The substances were administered orally and intraperitoneally.

The $LD_{50}$ was calculated in accordance with the method of L. C. MILLER and M. L. TAINTER, Proc. Soc. exper. Biol. Med., 1944, 57, 261.

By way of illustration and not of limitation, a few results are set forth.

| Compounds | $LD_{50}$ orally mg/kg | $LD_{50}$ intraperitoneally mg/kg |
|---|---|---|
| ST 729 | >1000 | 200 |
| ST 746 | 1000 | 300 |
| ST 761 | 1500 | 400 |

These derivatives are relatively non-toxic. The $LD_{50}$'s upon oral administration are greater than 1000 mg/kg for ST 767 - 771 - 776 - 778 - 790 and 811.

(B) Pharmacodynamics

The analgesic activity was studied in accordance with SIEGMUND et al. (J. Pharma. Exptl. Ther. 1957, 119, 453).

The compounds are administered orally 30 minutes before the injection of phenyl benzoquinone.

| Compounds | $ED_{50}$ mg/kg |
|---|---|
| Glaphenine | 36 |
| Acetylsalicylic acid | 100 |
| ST 729 | 1 |
| ST 746 | 100 |
| ST 761 | 4 |

The $ED_{50}$'s of the derivatives ST 767, 776, 778, 790 and 811 are between 1 and 50 mg/kg which, taking their low toxicity into account, leads to therapeutically high indices.

This activity had been confirmed from the testing of the electric stimulation of dental pulp in rabbits, in accordance with J. CHEYMOL et al., Therapie, 1959, 14, 350, in the case of derivatives ST 729 and ST 776. These derivatives are without ulcerogenic effect, in accordance with the criteria of C. J. PFEIFER and L. G. LEWALDOWFKI (Arch. Int. Pharmacodyn. 1971, 190, 5-13).

(C) Therapeutic Applications

Taking into consideration the perfect tolerance and the absence of secondary effects, clinical tests were carried out for certain chemical compounds which form the object of the invention.

They were applied in the case of stubborn pains, particularly those amenable to prolonged treatment. The results obtained have proven satisfactory.

The pharmaceutical preparations containing these active principles can be administered orally, parenterally, or rectally.

For oral administration, capsules, tablets, and/or elixirs can be used.

The individual dose is between 50 and 200 mg. with a maximum daily dose of 1000 mg.

These pharamecutical compositions may also contain other pharmaceutically and therapeutically acceptable active principles. A few examples of pharmaceutical preparations containing some of the active principles which are the object of experimentation are given below, by way of illustration and not of limitation:

| | |
|---|---|
| (a) Tablets: | |
| ST 729 | 50 mg |
| Excipient: lactose. | |
| (b) Capsules | |
| ST 776 | 50 mg |
| Meprobamate | 100 mg |
| (c) Tablets | |
| ST 811 | 50 mg |
| L-arginine | 150 mg |
| per sugar-coated pill | |
| (d) Injectible ampules | |
| Hydroxo cobalamine base | 10 mg |
| ST 811 | 20 mg |
| Independent phosphate buffer solution to make up 2 ml. | |
| (e) Children's suppositories | |
| ST 729 | 50 mg |
| Semi-synthetic glycerides q.s.p. 1 suppository of 1 g. | |
| (f) Adult suppositories | |
| ST 729 | 100 mg |

What is claimed is:

1. A chemical compound selected from the group having the formula:

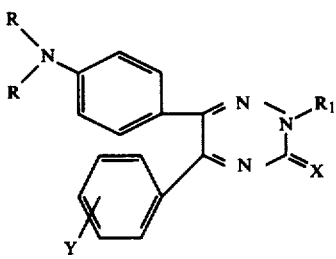

in which:
R is a lower alkyl
R₁ is lower alkyl, allyl, aminoalkyl of the type

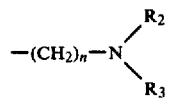

in which n=2 to 4 and R₂R₃ represent lower alkyl and may also form a heterocycle with the nitrogen atom, in which the carbon chain may be uninterrupted or interrupted by a single oxygen atom so as to form a morpholine radical with the oxygen in the 4 position thereof Y is hydrogen, halogen, lower alkyl, or

wherein R is lower alkyl,
X=an oxygen or sulfur atom and salts thereof with therapeutically acceptable organic or inorganic acids.

2. A compound according to claim 1, which is 2-methyl 3-oxo 5,6 di(paradimethylamino phenyl) as triazine.

3. A compound of claim 1 which is 2-methyl-3-oxo-5,6-di(para-diethylaminophenyl) as triazine.

4. A compound of claim 1 which is 2-methyl 3-oxo 5(orthochlorophenyl) 6(p-dimethylaminophenyl) as triazine.

5. A compound of claim 1 which is 2-methyl 3-oxo 5(p-chlorophenyl) 6(p-dimethylaminophenyl) as triazine.

6. A compound of claim 1 which is 2-ethylmorpholine 3-oxo 5,6-di(para-dimethylaminophenyl) as triazine.

7. A compound of claim 1 which is 2-allyl 3-oxo 5,6-di(para-dimethylaminophenyl) as triazine.

8. A compound of claim 1 which is 2-[3-(dimethylamino)propyl]3-oxo 5,6-di(para-dimethylaminophenyl) as triazine.

9. A compound of claim 1 which is 2-diethylaminoethyl 3-oxo 5,6-di(para-dimethylaminophenyl) as triazine.

10. A compound of claim 1 which is 2-methyl 3-thione 5,6-di(para-dimethylaminophenyl) as triazine.

11. The method of treating rheumatic disturbances and pains in an individual subject thereto which comprises the step of treating the said individual with a compound according to claim 1 in an amount effective for such purpose.

12. The method of claim 11, wherein the amount of active ingredient is between about 50 and 1000 milligrams.

13. The method of treating rheumatic disturbances and pains in an individual subject thereto which comprises the step of treating the said individual with a compound according to claim 2 in an amount effective for such purpose.

14. The method of claim 13, wherein the amount of active ingredient is between about 50 and 1000 milligrams.

15. A pharmaceutical composition useful in the treatment of rheumatic disturbances and pains comprising a compound of claim 1 in admixture with a pharmaceutically-acceptable carrier or excipient.

16. A pharmaceutical composition of claim 15, wherein the amount of active ingredient is between about 50 and 200 milligrams.

17. A pharmaceutical composition useful in the treatment of rheumatic disturbances and pains comprising a compound of claim 2 in admixture with a pharmaceutically-acceptable carrier or excipient.

18. A pharmaceutical composition of claim 17, wherein the amount of active ingredient is between about 50 and 200 milligrams.

19. A pharmaceutical composition of claim 15 in a form suitable for administration orally, rectally, or parenterally.

20. A pharmaceutical composition of claim 17 in a form suitable for administration orally, rectally, or parenterally.

21. Method of claim 11, wherein the compound is administered orally, rectally, or parenterally.

22. Method of claim 13, wherein the compound is administered orally, rectally, or parenterally.

23. Method of claim 11, wherein the compound is 2-methyl-3-oxo-5,6-di(para-diethylaminophenyl) as triazine.

24. A pharmaceutical composition of claim 15, wherein the compound is 2-methyl-3-oxo-5,6 di(para-diethylaminophenyl) as triazine.

* * * * *